United States Patent [19]

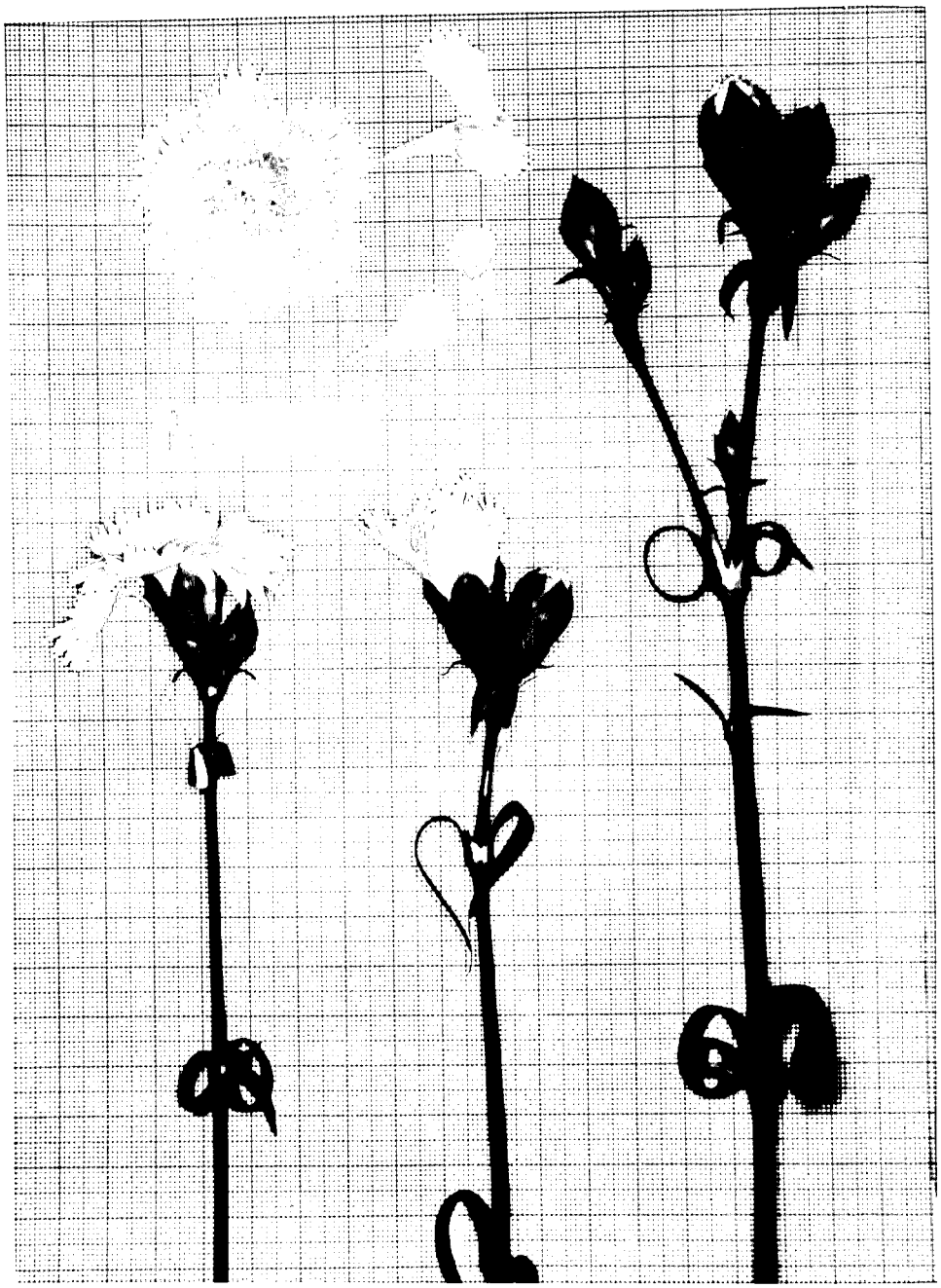

Nobbio

[11] Patent Number: Plant 5,766

[45] Date of Patent: Jul. 15, 1986

[54] CARNATION NAMED MEI-FU

[76] Inventor: Giacomo Nobbio, Strada Villetta 5, San Remo, Imperia, Italy

[21] Appl. No.: 600,943

[22] Filed: Apr. 16, 1984

[51] Int. Cl.[4] ..... A01H 5/00

[52] U.S. Cl. ..... Plt./70

[58] Field of Search ..... Plt./70–73

*Primary Examiner*—James R. Feyrer

*Attorney, Agent, or Firm*—Charles W. Rummler

[57] ABSTRACT

A new carnation cultivar particularly distinguished by its relatively small, double type, pink and white flowers, the petals of which are generally fan shaped and have a base coloration of several shades or tones of pink spreading outwardly from the base to a deeply serrated white margin, on the upper side, and having an homogeneous white coloration on the under side lightly tinged with the pink ground color of the upper side, the flowers being of symmetrical shape and of rather flat form borne on sturdy stems of medium thickness and very elastic.

1 Drawing Figure

BACKGROUND OF THE NEW PLANT

This new carnation cultivar originated as a seedling in 1980 at my breeding establishment in San Remo, Italy, resulting from my crossing of an unnamed variety, as the seed parent, identified under U.S. Plant Pat. No. 829 in my breeding records, with an unnamed variety identified in my records under U.S. Plant Pat. No. 810, as the pollen parent, both parents being generally pink in color with white edging. This seedling was selected for propagation because of the several pink color tones in the upper surface of the flower petals, each of which is in the form of a fan exhibiting an irregular corona overlaid with a faint pink coloration, the ground color of the petals spreading out fanwise over the entire petal surface with the exception of deeply serrated, irregular white petal margins. Repeated trials of propagation of this seedling, by means of cuttings, demonstrated that the novel characteristics of the parent plant held true from generation to generation and appeared to be firmly fixed.

DESCRIPTION OF THE DRAWING

This new carnation variety is illustrated by the accompanying full color photographic drawing, which shows the inflorescence of a fully grown plant, the view including buds in various stages of opening, as well as a face view of a fully opened flower, specimens of the upper and reverse side of the flower petals, and specimens of pinched and unpinched flowering stems, the color rendition being as nearly true as it is reasonably possible to obtain by conventional photographic procedures and the manner in which the subjects are displayed for photography.

DESCRIPTION OF THE NEW PLANT

The following is a detailed description of my new carnation variety based upon observation of plants growing under conventional greenhouse procedures, the color designations being according to The R.H.S. Colour Chart of The Royal Horticultural Society of London, England.

THE PLANT

Origin: Seedling.

Parentage:

*Seed parent.*—Unnamed variety identified in my records under U.S. Plant Pat. No. 829.

*Pollen parent.*—An unnamed variety identified in my records under U.S. Plant Pat. No. 810. Both parents are of a general pink color with white edging of the flower petals.

Classification:

*Botanic.*—*Dianthus caryophyllus.*

*Commercial.*—Greenhouse carnation for cut flower production.

Form: Herbaceous bush.

Height: Short, with sturdy stems each having seven internodes visible immediately under the flower, the stems being of medium thickness and very elastic with rounded and irregularly fluted cross-section in the middle of the longest internode.

Growth: Vigorous and upright.

Branching: Normal and medium in number. The initial 30 to 40 cm. stem is pinched at about 10 to 15 cm. to cause the formation of 4 or 5 shoots and subsequent branching of the shoots which may be suitably pinched for the desired flower production.

Foliage:

*Quantity.*—Moderate.

*Leaf size.*—Moderate, of medium length and medium breadth.

*Leaf shape.*—Linear and irregular with entire margins and a strong tendency to curl under in a disparate manner.

*Texture.*—Smooth.

*Color.*—Green.

THE BUD

Size: Medium.

Form: Generally ovoid until color appears and then becoming progressively cylindrical as the flower opens.

Sepals:

*Condition.*—Upstanding and pointed and of a lighter green color than the stem.

Calyx:

*Length.*—Short.

*Shape.*—Bell-shaped.

*Nature.*—The outer calyx is almost always formed from four bracts.

*Aspect.*—Smooth.

THE FLOWER

Blooming habit: Continuous.

Size of bloom: Small and of double type about 4 to 4.5 cm. in diameter.

Borne: On strong, upright stems with tendency toward being racemose with plural buds unless disbudded.

Shape: Symmetrical and flat.

Petalage:

*Number.*—20 to 39.

*Arrangement.*—Generally imbricated.

*Shape.*—Fan-shaped with serrated margin.

*Color.*—Upper side of petals: Generally Pink, R.H.S. 55A overall, the hue being of four tones deepest at the base and lightening progressively toward the petal margin, the serrated margin being White, R.H.S. 155D, and each petal having an irregular corona pattern of color between R.H.S. 53B and R.H.S. 53C at the outermost point of the claw. Under side: Generally overall white with slight tinging of pink.

*Texture.*—Soft.

*Appearance.*—Satiny.

Fragrance: Faint.

Persistence: The petals hang on and dry.

Lasting quality: As a cut flower, the endurance is excellent and has excellent suitability for shipment.

REPRODUCTIVE ORGANS

Androecium: Absent during the winter period.

Styles: Not more than two.

Stamens: None.

Pistils:

*Number.*—Two.

*Styles.*—Length: Medium. Color: White.

*Ovaries.*—Smooth and egg-shaped.

*Size.*—Short, about 15 mm. in length with medium slenderness.

*Color.*—White.

Stigma:

*Surface.*—Smooth.

Ovary: Cylindrical in shape.

I claim:

1. A new and distinct variety of carnation, substantially as herein shown and described, characterized by its relatively small, double type flowers of symmetrical and flat shape, and by the several color tones on the upper surface of the flower petals which spread as on a fan, the petals also exhibiting an irregular corona pattern of color and a white reverse side which is overlaid by a faint pink coloration.

* * * * *

UNITED STATES PATENT AND TRADEMARK OFFICE

CERTIFICATE OF CORRECTION

PATENT NO. : Plant 5,766

DATED : July 15, 1986

INVENTOR(S) : Giacomo Nobbio

It is certified that error appears in the above-identified patent and that said Letters Patent are hereby corrected as shown below:

Column 1, line 6, delete "U.S. Plant Pat.".

Column 1, line 8, delete "U.S. Plant Pat.".

Column 2, line 3, delete "U.S. Plant Pat.".

Column 2, line 5, delete "U.S. Plant Pat.".

Signed and Sealed this

Twenty-first Day of October, 1986

[SEAL]

*Attest:*

DONALD J. QUIGG

*Attesting Officer*

*Commissioner of Patents and Trademarks*